(12) United States Patent
Frick et al.

(10) Patent No.: US 7,538,871 B2
(45) Date of Patent: May 26, 2009

(54) COLOUR MEASUREMENT DEVICE WITH ASSOCIATED MEASUREMENT HEAD

(75) Inventors: Beat Frick, Buchs (CH); Adrian Von Orelli, Zürich (CH)

(73) Assignee: X-Rite Europe GmbH, Regensdorf (CH)

( * ) Notice: Subject to any disclaimer, the term of this patent is extended or adjusted under 35 U.S.C. 154(b) by 223 days.

(21) Appl. No.: 11/355,140

(22) Filed: Feb. 15, 2006

(65) Prior Publication Data

US 2006/0192957 A1      Aug. 31, 2006

(30) Foreign Application Priority Data

Feb. 16, 2005   (CH)   .................... 00264/05
Feb. 28, 2005   (CH)   .................... 00339/05

(51) Int. Cl.
*G01J 3/28*   (2006.01)
(52) U.S. Cl. .................. 356/326; 356/446; 356/402
(58) Field of Classification Search ................ 356/328, 356/402–425, 446; 385/1.9
See application file for complete search history.

(56) References Cited

U.S. PATENT DOCUMENTS 6,384,918 B1 *   5/2002   Hubble et al. ............... 356/402

2002/0122192 A1 *   9/2002   Ott ............................ 358/1.9
2005/0052648 A1   3/2005   Frick et al.
2006/0024007 A1 *   2/2006   Carlin et al. ................. 385/117

FOREIGN PATENT DOCUMENTS

EP         1507134      2/2005

* cited by examiner

*Primary Examiner*—Kara E. Geisel
*Assistant Examiner*—Abdullahi Nur
(74) *Attorney, Agent, or Firm*—McCarter & English, LLP

(57) ABSTRACT

A spectrophotometer for integration purposes includes a measurement head with an illumination arrangement (10) including at least one fight source (11) for the illumination of a measurement object located in a measurement plane (M) under an angle of incidence of at least 45°, with a pick-up arrangement for capturing the measurement light remitted by the measurement object under an angle of reflection of the essentially 0° relative to the perpendicular of the measurement plane, a spectrometer arrangement (30) with an entry slot (31) for the spectral splitting of the measurement fight received through the entry slot and captured and with a photoelectric receiver arrangement (32) exposed to the spectrally split measurement light for conversion of the individual spectral portions of the measurement light into corresponding electrical signals.

31 Claims, 10 Drawing Sheets

Figure 1:
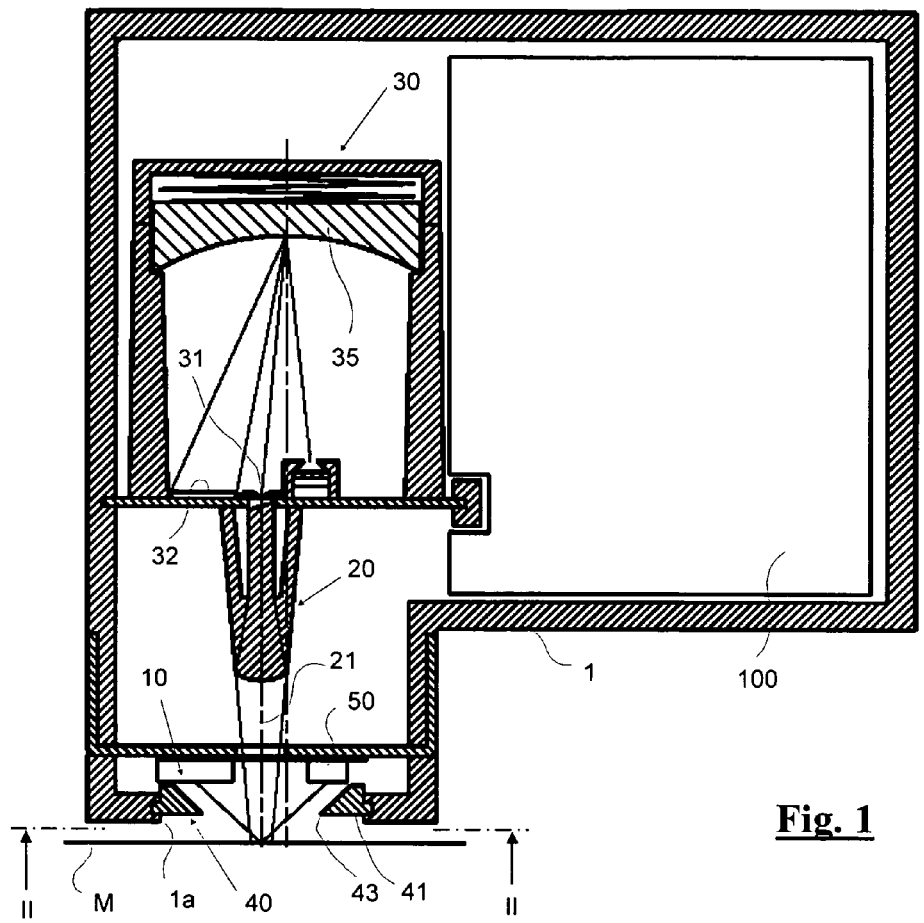

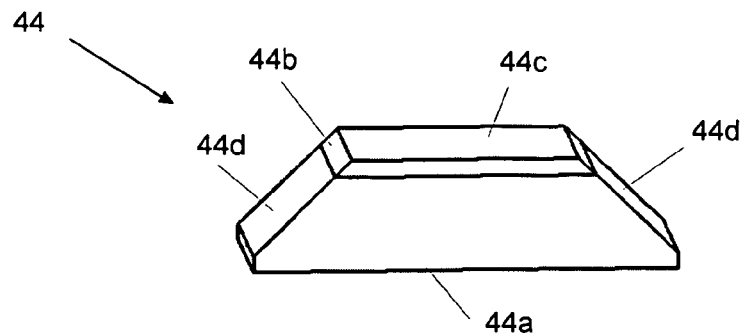
Fig. 4
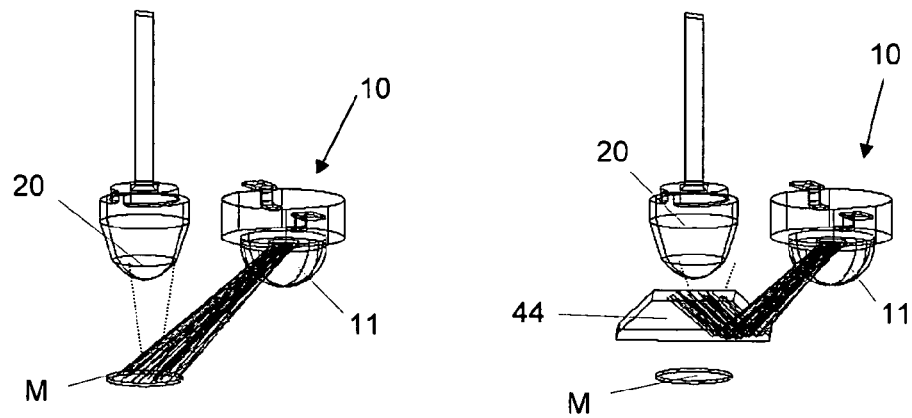
Fig. 5a      Fig. 5b
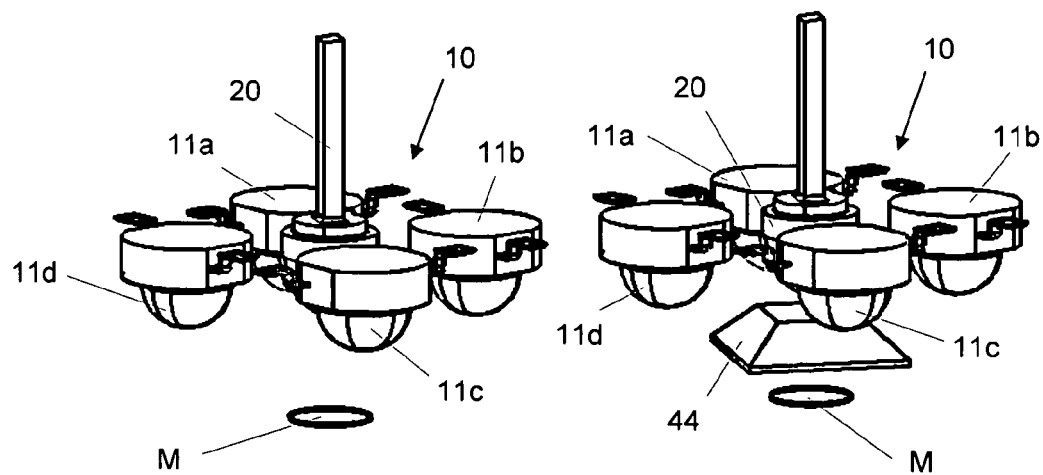
Fig. 6a      Fig. 6b

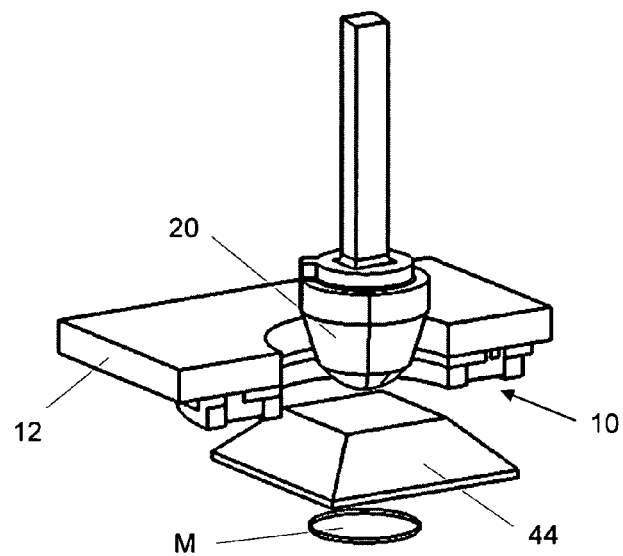
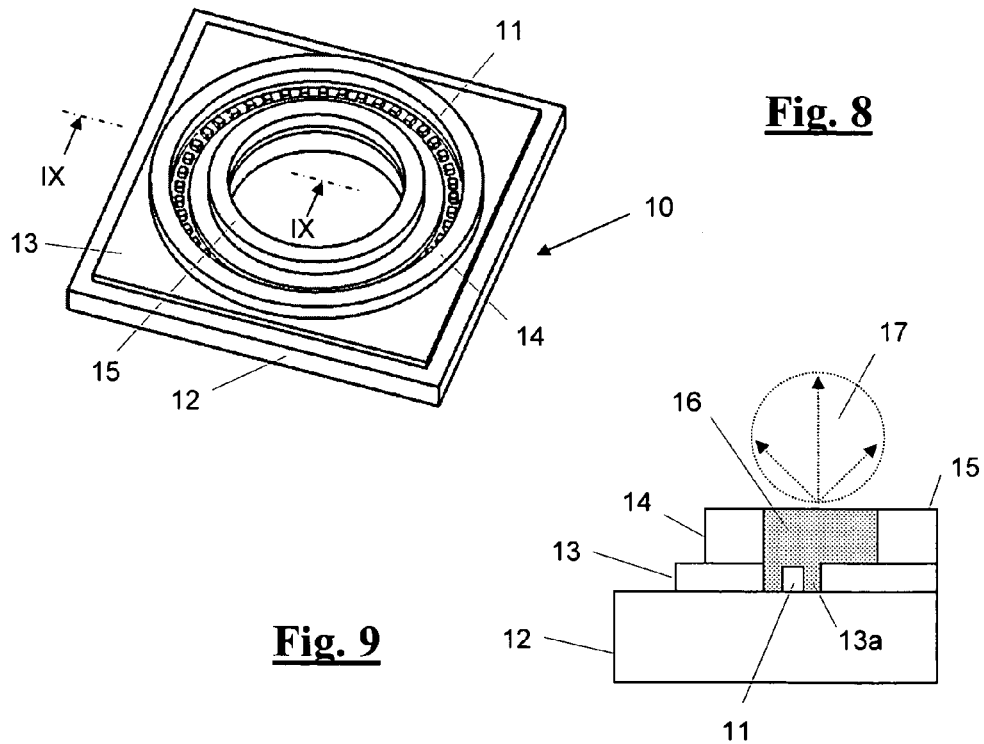

COLOUR MEASUREMENT DEVICE WITH ASSOCIATED MEASUREMENT HEAD

The invention relates to a measurement head for a colour measurement device as well as a colour measurement device equipped with an advantageous measurement head.

More concretely, the invention relates to improvements of various detailed aspects of a colour measurement device suited for incorporation into colour enabled reproduction devices, especially colour printers, in particular spectrophotometers of the type described, for example, in EP-A 1 507 134 (corresponding to U.S. patent application Ser. No. 10/894,797 of Jul. 20, 2004).

For the characterization, ink limitation, linearization and profiling of ink jet printers, colour charts (so called Test Charts) are printed and subsequently measured with a manual or automatic colour measurement device. Spectrometers with 45°/0°-geometry are thereby used as colour measurement devices, the data used are typically L*a*b* or spectral remissions in the range of 380 nm to 730 nm. Suitable colour measurement devices are for example the devices "Spectrolino" and "i1" of the company Gretag-Macbeth AG, Regensdorf, Schweiz.

Ink limitation or linearization are typically included in the software of the printer, whereby certain printers, for example, of the companies Hewlett-Packard and Xerox, also already include built-in sensors with densitometer functions for the automatic linearization.

ICC Profiles are generally generated by way of a colour management software (for example "Profile Maker" of the company Logo GmbH) on the basis of the measurement data of the colour charts.

Ink limitation, linearization and profiling are depended on different influencing factors, for example, the condition of the printing head, the paper type and paper batch, the ink type and ink batch, the printing modus, printer registration, environmental conditions such as temperature and humidity. Pre-adjusted parameters are generally used for the ink limitation and linearization. The deviations from the nominal which result from the tolerances of media batches and the environmental conditions are compensated by the profile. Generic and pre-adjusted profiles for all possible combinations of media and printing modes are, however, not always sufficient, which is why in the practice local profiles are additionally manually produced and used for higher quality demands.

In order to simplify these activities, it would be desirable to provide a colour printer with an integrated measurement device so that the complete characterization (ink limitation, linearization, profiling) for all media (ink, paper) can be carried out without additional auxiliary devices and manual measurement processes.

A suitable measurement device for this use must comply with very high demands. Apart from the normal demands with respect to standardized measurement geometry, spectral region, position and consistency (repeatability of measurement results) it must be able to deliver spectral data, colorimetric data and standardized or specific colour density data. These demands can definitely be fulfilled with the currently commercially available spectrophotometers, for example, the above-mentioned devices "Spectrolino" and "i1" of the company Gretag-Macbeth AG. However, there are further limitations on a integrated device with respect to the integration size (compact shape) and possibly the weight. Furthermore, additional demands exist with respect to environmental conditions (temperature, humidity) and the danger of contamination in the vicinity of the printing mechanics (dust, color fog, etc.). Furthermore, the measurement cannot be carried out in direct physical contact with a medium, since the print, for example with ink-jet printers, is still wet and mechanically sensitive for certain amount of time. An integrated device must also be insensitive to mechanical vibrations and must have long lived light sources. Since the distance to the measurement object is subject to variations because of the unacceptable direct physical contact with a measurement device, the measurement object must also be able to handle those. Finally, service friendliness and commercial criteria also play a significant role, since such measurement devices are needed in high numbers and therefore must be manufactureable relatively cheaply. It is especially required that the assembly can be carried out with low installation and adjustment effort.

The spectrophotometer described in EP-A 1 507 134 (corresponding to U.S. patent application Ser. No. 10/894,797 of Jul. 20, 2004) mainly complies with the above-mentioned requirements, but can be improved in some aspects.

The present invention is now to provide a colour measurement device, especially a spectrophotometer or a measurement head for a colour measurement device, especially spectrophotometers of the generic type with respect to performance, precision, relative simplicity of manufacture and multiplicity of possible uses.

This object of the invention is now achieved with the measurement head in accordance with the invention characterized by the features of the claimed measurement head and colour measurement device set forth herein.

Preferred embodiments and further developments of the measurement head in accordance with the invention and the colour measurement device in accordance with the invention are the subject of the depended claims.

Figure 3B:
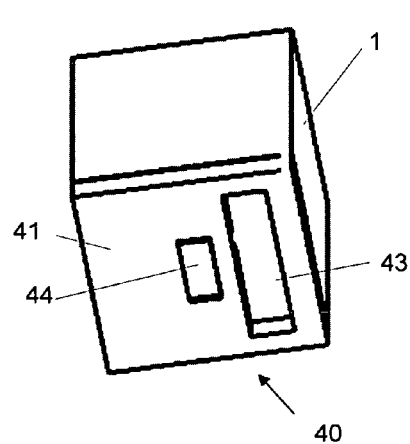
Figure 3A:
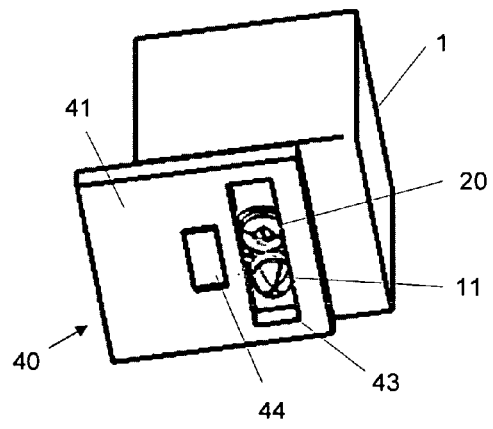
Figure 2B:
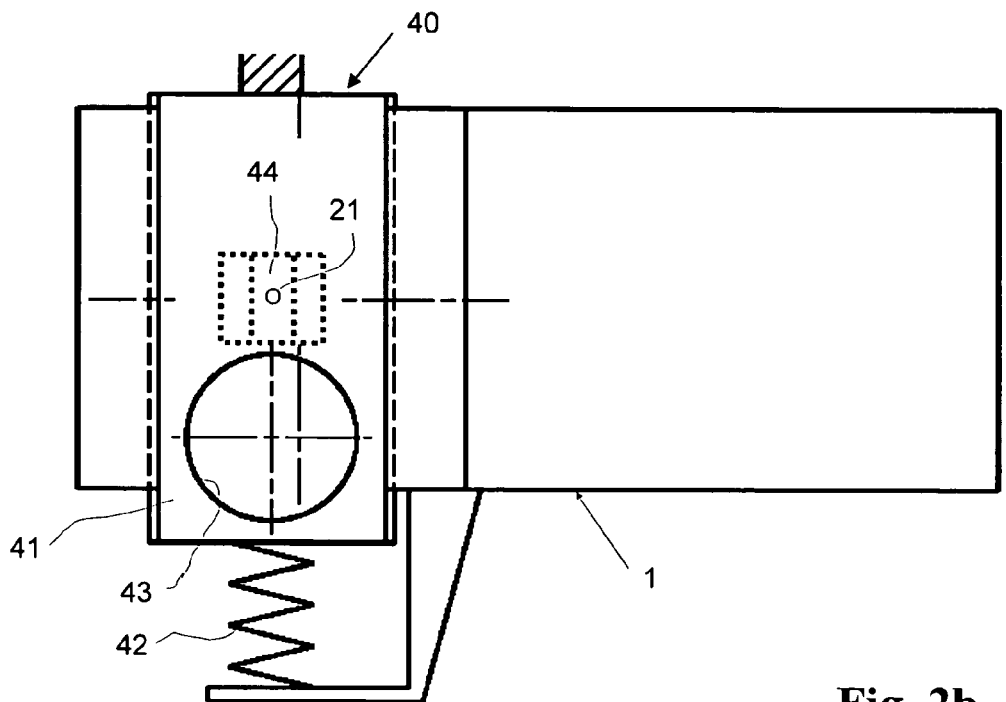
Figure 2A:
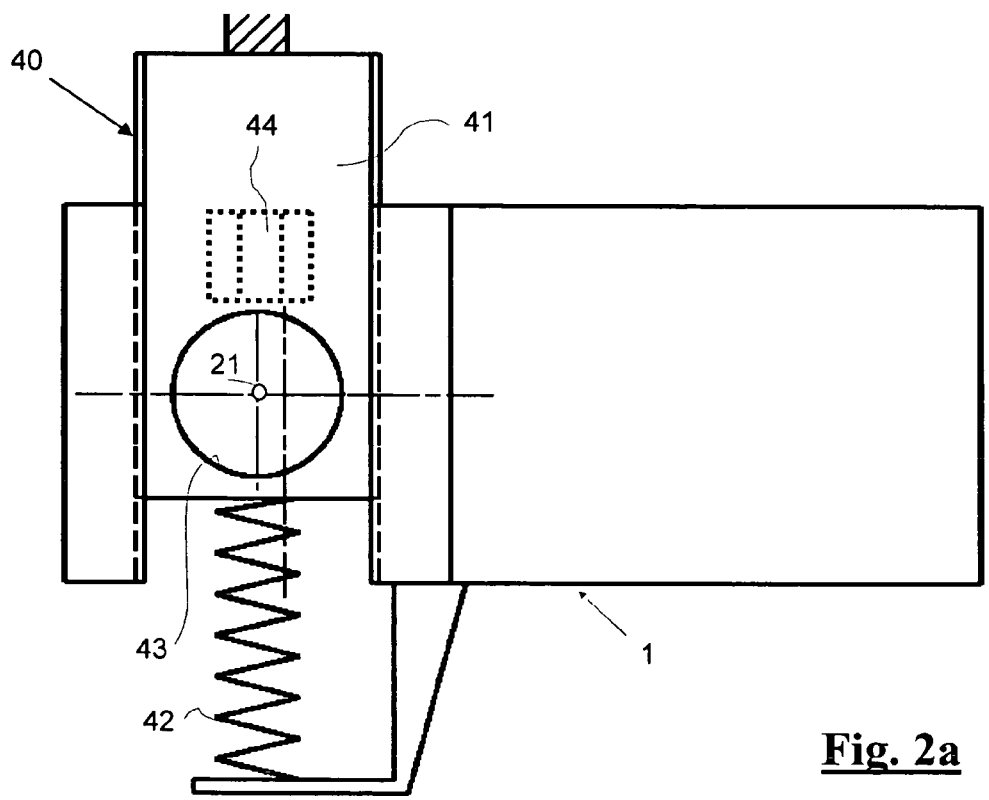
Figure 10:
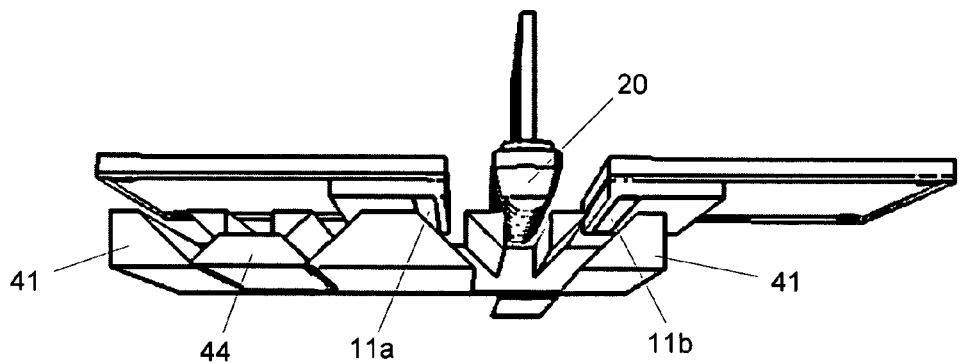
Figure 11:
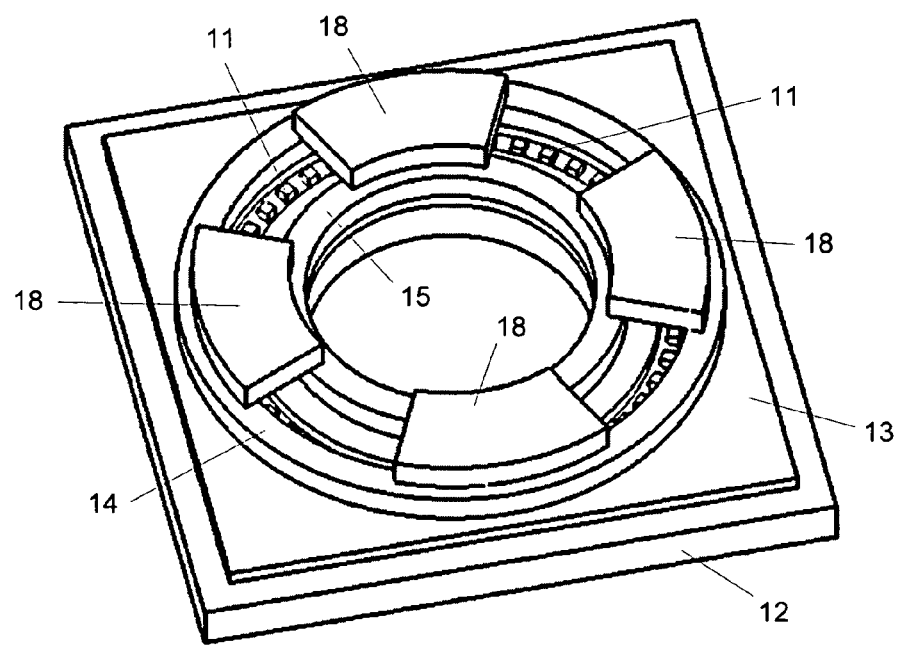
Figure 12:
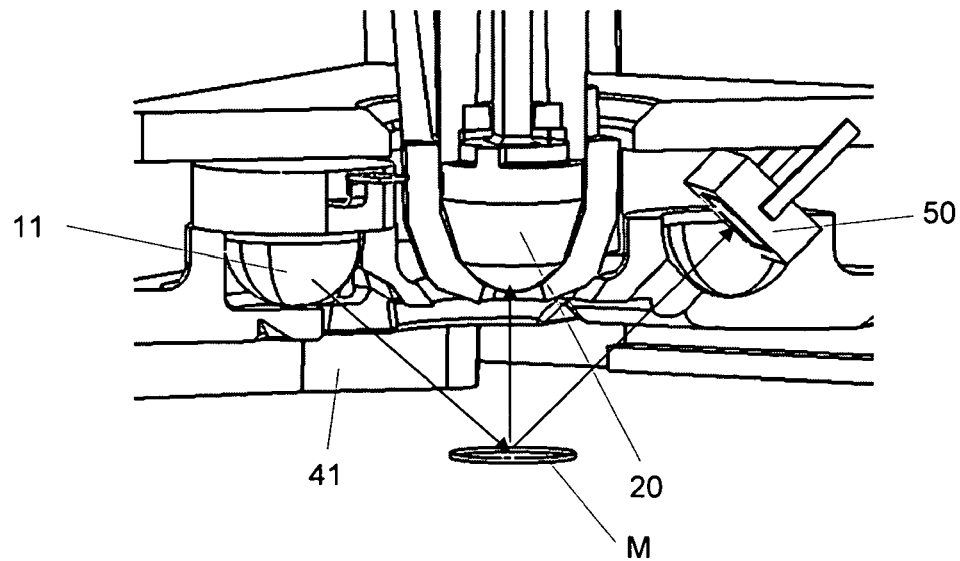
Figure 13:
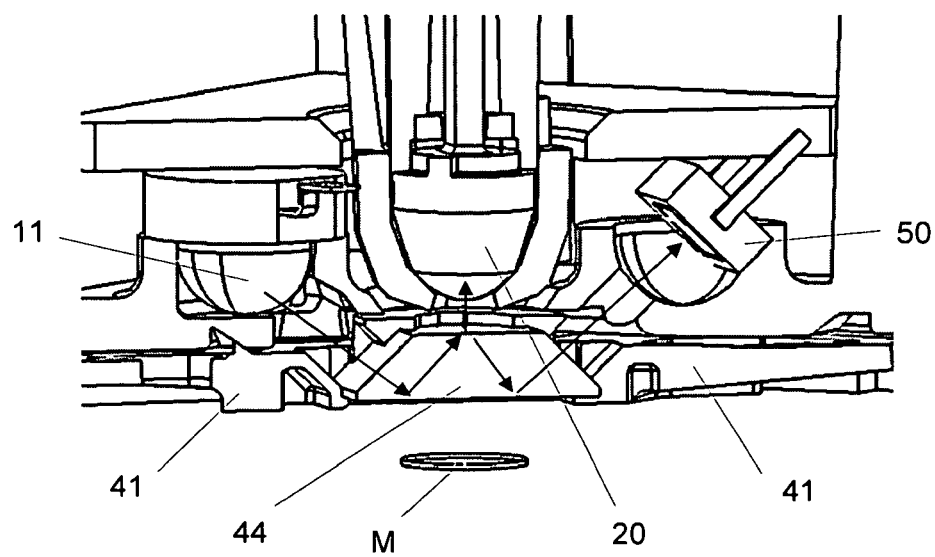
Figure 14:
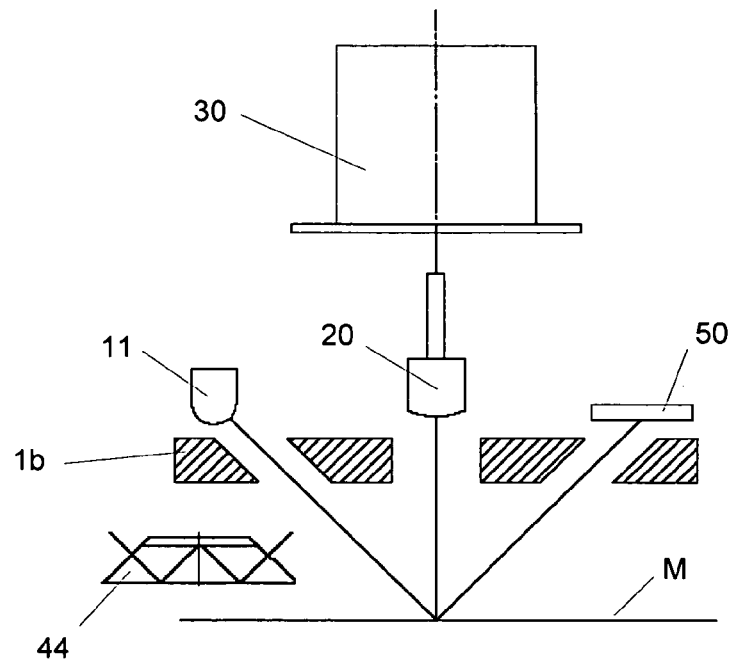
Figure 15:
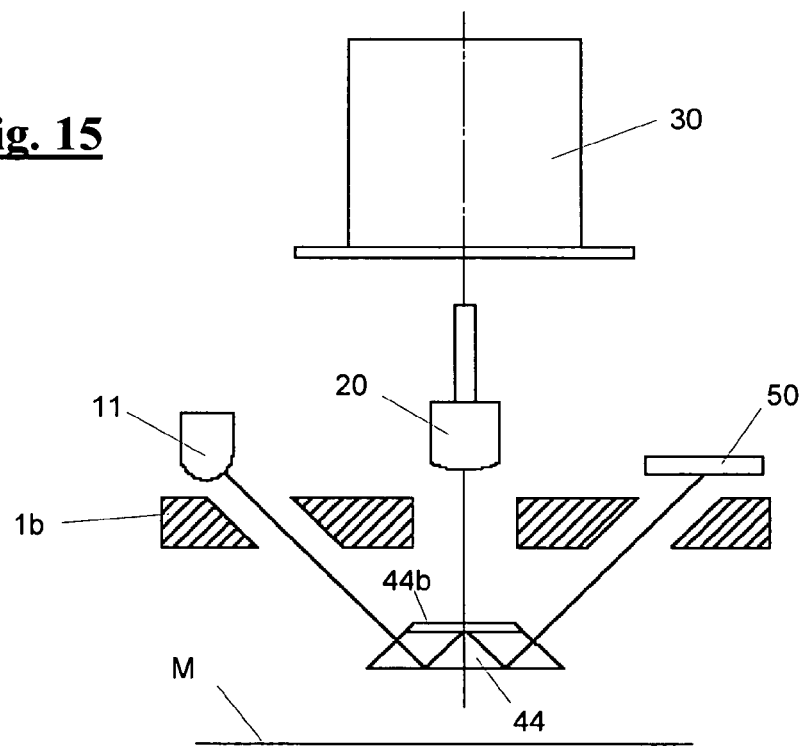
Figure 18:
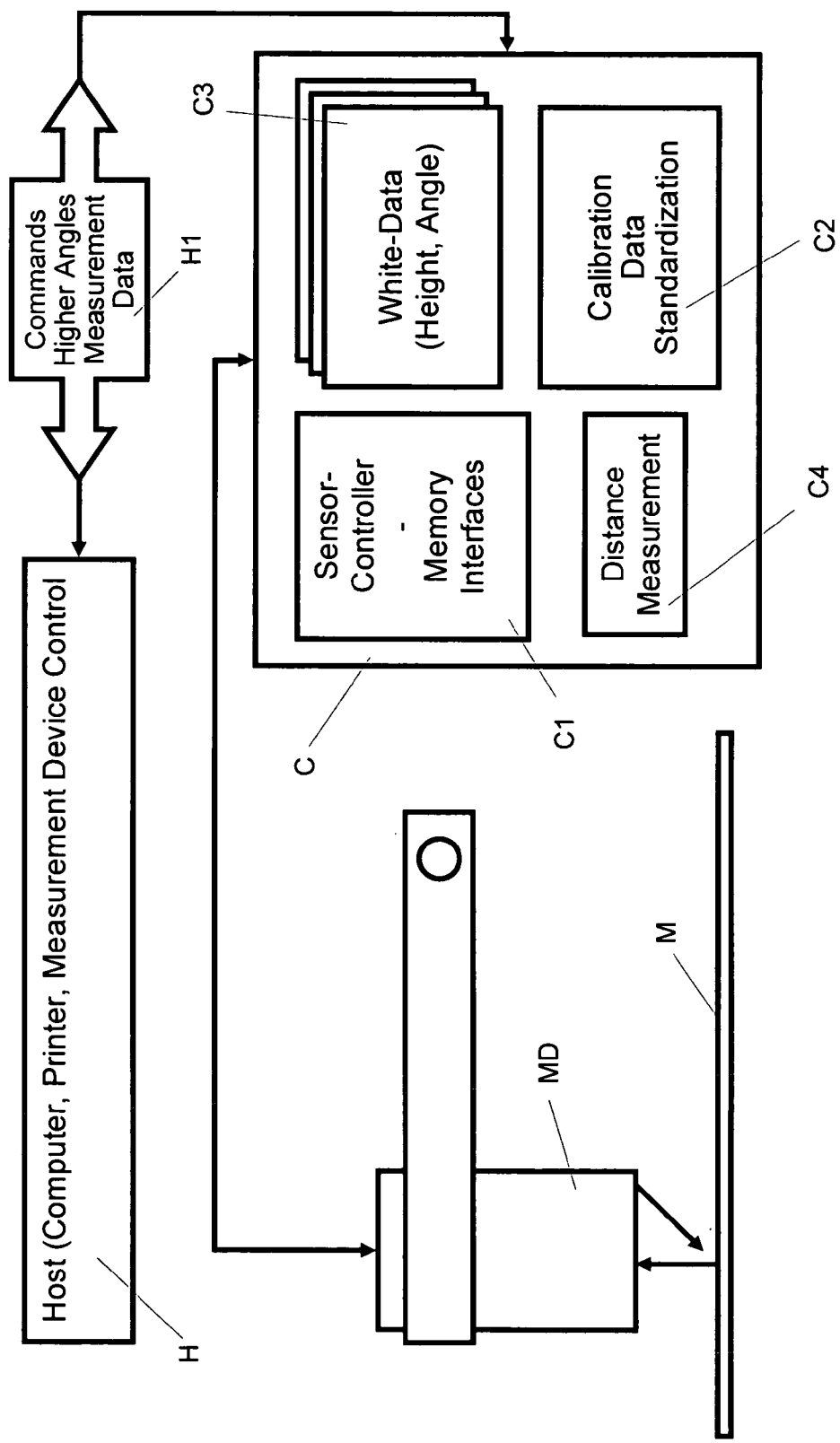
Figure 19A:
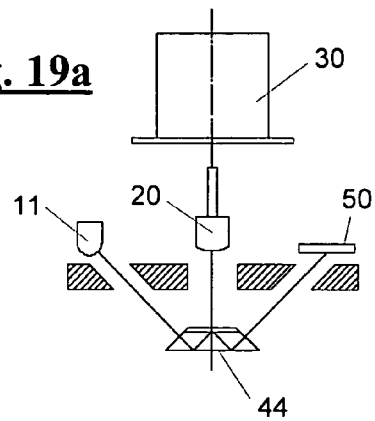
Figure 19B:
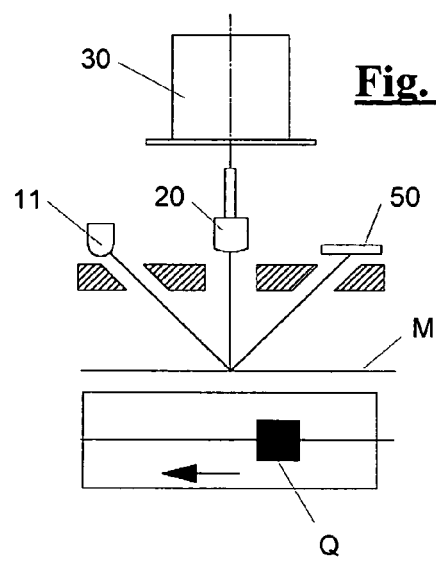

The invention will be further described in the following with reference to the drawings. It shows:

FIG. 1 a longitudinal section through an exemplary embodiment of the colour measurement device in accordance with the invention, here constructed as a spectrophotometer;

FIGS. 2*a-b* two views according to line II-II in FIG. 1;

FIGS. 3*a-b* each a view of a practical variant of a brightness reference arrangement of the colour measurement device in two different working positions;

FIG. 4 an exemplary embodiment of a redirecting arrangement;

FIGS. 5*a-b* each a principle sketch for the illustration of the function of the redirecting arrangement;

FIGS. 6*a-b* each a principle sketch for the illustration of a variant of the redirecting arrangement;

FIG. 7 the redirecting arrangement of FIGS. 6*a-b* in connection with an annular illumination arrangement;

FIG. 8 a view of an exemplary embodiment of an annular illumination arrangement;

FIG. 9 a section along line IX-IX in FIG. 8;

FIG. 10 a view of the components relevant to the invention of a linear scanning arrangement;

FIG. 11 a variant of the annular illumination arrangement according to FIG. 8;

FIG. 12-13 each a partial view of the colour measurement device in the practical use for the gloss measurement in two different positions of the brightness reference arrangement;

FIGS. 14-15 each a schematic illustration according to FIGS. 12 and 13;

FIGS. 16*a-d* a colour measurement head in four typical measurement situations during its standardization;

FIGS. 17*a-d* a colour measurement head in four typical measurement situations in the practical use;

FIG. 18 a schematic of various functional units of the colour measurement device;

FIG. 19a-b two sketches for the illustration of a distance measurement; and

Figure 20A:
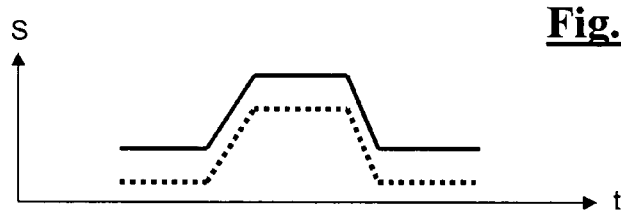
Figure 20B:
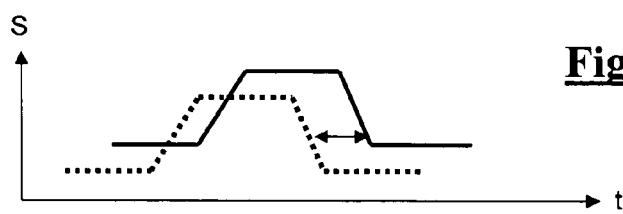
Figure 20C:
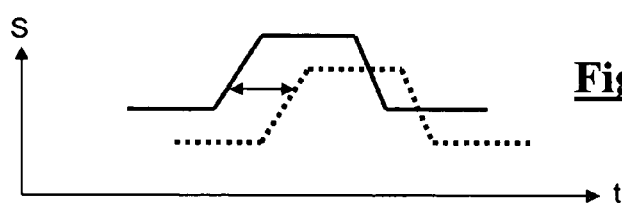

FIGS. 20a-c three measurement signal curves typically occurring in different situations during the distance measurement.

Colour measurement device in the following is understood to refer to a type of measurement device which in the widest sense determines a colour information of the measurement object by photoelectric scanning. This includes spectrophotometers, colorimeters, colour density measurement devices, etc. Although the invention is in the following described by way of the example of a spectrophotometer, it is in no way limited thereto.

The colour measurement device illustrated in FIG. 1 is constructed as a spectrophotometer, for example, and includes an outer housing 1 in which all mechanical, optical and electrical components are housed. The housing 1 has at its lower end (in the drawing) an opening 1a during which the measurement beam passes during operation. When not in operation, the opening 1a is closed by a brightness reference arrangement 40 which at the same time acts as a closure, which will be described in detail further below. The measurement plane in which an object to be measured is located in the practical operation, is referred to by M. In several figures, M also refers to the illuminated measurement spot on the measurement object.

The components of the spectrophotometer are apart from the already mentioned brightness reference arrangement 40, an illumination arrangement 10 for the illumination of the measurement object in the measurement plane M at an angle of incidence of essentially 45°, a pick-up arrangement 20 for the capture of the measurement light remitted from the measurement object at an angle of reflection of essentially 0° relative to the perpendicular of the measurement plane M, a spectrometer arrangement 30 with a concave refraction grating 35 for the spectral splitting of the measurement light captured by the pick-up arrangement 20 and guided thereto through an entry gap 31, a photoelectric receiver arrangement 32 provided within the spectrometer arrangement 30 and impinged by the spectrally split measurement light, for the conversion of the individual spectral portions of the measurement light into corresponding electrical signals and an electronic control 100, which controls the illumination arrangement 10 or the light source(s) 11 included therein and generates digital measurement values (spectral data, colour data, colour density data, etc.) from the electrical signals produced by the photoelectric receiver arrangement 32 in combination with standardization and calibration data and makes them available for further use at a not illustrated digital interface. A further photoreceptor 50 connected with the electronic control 100 is positioned opposite the light source(s) 11 for the capture of the light reflected from the measurement object (gloss), which receives the measurement light reflected from the measurement object at an angle of reflection of essentially 45° according to standard.

The already mentioned brightness reference arrangement 40 is provided instead of the white tile normally common in the spectrophotometers and other colour measurement devices and used for the relative white calibration, which brightness reference arrangement is positioned at a relatively large distance of typically about 2 mm above the measurement plane M. The brightness reference arrangement consists essentially of a sled 41 which is moveable in the opening 1a of the outer housing 1 transverse to the optical axis 21 of the pick-up arrangement 20 between a measurement position and a reference position, as is apparent from the two FIGS. 2a (measurement position) and 2b (reference position). The translation in the reference position is carried out, for example, by an external, not illustrated drive, against the force of a spring 42, which holds the sled 41 in the measurement position or moves it back into the measurement position upon disappearance of the external force. Of course, the translation of the sled 41 can also be carried out in both directions by an external force, whereby the spring 42 is then not required.

The sled 41 is provided with a cut-out or passage 43 which is of sufficient size so that in the measurement position of the sled 41 (FIG. 2a) the illumination light and the measurement light remitted from the measurement object can pass unimpeded (FIG. 1).

A redirecting arrangement 44 is mounted on the sled 41 and offset in the direction of movement from the passage 43, which redirecting arrangement lies in the illumination and pick-up beam path in the reference position of the sled 41 and guides the illumination light into the pick-up arrangement 20. The concrete construction of the redirecting arrangement is described in detail further below.

The colour measurement device, or here especially the spectrophotometer, is closed to the outside in the reference position of the sled 41. Therefore, the brightness reference arrangement 40 functions at the same time as a mechanical and optical closure (the latter, for example, for darkness measurement). Furthermore, the spacing between the spectrophotometer and the measurement object is maintained and the brightness reference arrangement is accommodated within the enclosed space of the spectrophotometer.

To this point, the colour measurement device in accordance with the invention or specifically the spectrophotometer, corresponds in principle concept and function essentially to the spectrophotometer described in all details in EP-A 1 507 134 (corresponding to U.S. patent application Ser. No. 10/894, 797 of Jul. 20, 2004), so that the person skilled in the art does not need any further explanation in relation thereto. Details of the electronic control 100 are also described in the above-mentioned EP and U.S. applications. The differences between the colour measurement device in accordance with the invention and this prior art reside in the specific construction and design of the individual components, especially the brightness reference arrangement 40 and the illumination arrangement 10, which will be discussed further in the following.

A practical realization variant of the brightness reference arrangement 40 is shown in FIGS. 3a and 3b in measurement position (FIG. 3a) or in reference position (FIG. 3b) of the sled 41. In the open measurement position of FIG. 3a, the lens head of the pick-up arrangement 20 as well as a light emitting diode 11 of the illumination arrangement are apparent. In this realization variant, the sled 41 is moved in both directions by an externally applied force.

A first important aspect of the invention relates to the design of the redirecting arrangement 44 in the brightness reference arrangement 40.

In the simplest embodiment, the redirecting arrangement 44 consists of a prism shaped glass body with trapezoid cross-section which has a base surface 44a, a top surface 44c formed by the outer surface of a thin scattering layer 44b, two inclined side surfaces 44d and two not referenced lateral end surfaces. The two side surfaces 44d are at an angle of 45° to the base surface. The base surface 44a is mirrored, the two lateral surfaces are polished to be planar. The scattering layer 44b consists of a thin opal glass layer. The whole glass body is made of a so-called white flashed opal glass as is available from the company Schott AG under the name Opalika. White flashed opal glass is a double layer glass with a colourless (transparent) base layer and an evenly milky opaque cover layer homogeneously connected therewith. The cover layer thereby forms the scattering layer 44b found at the surface of the glass body.

The glass body 44 is mounted with its base surface 44a on the sled 41 so that the scattering layer 44b is directed towards the lens head of the pick-up arrangement 20. Base and cover surface are thereby perpendicular to the optical axis 21 of the pick-up arrangement 20 (FIG. 1), the two lateral surfaces 44d are inclined thereto at an angle of 45°.

FIGS. 5a and 5b show the practical use of the redirecting arrangement 44. In FIG. 5a, the sled is in the measurement position, whereby the light originating from the illumination arrangement 10 including here only one single light emitting diode 11, falls unimpeded onto the measurement spot M at 45°+/−5°. The light emitted from the measurement spot is captured by the pick-up arrangement at 0°+/−5° and then guided to the spectrometer arrangement (here not illustrated). In the reference position of the sled, the glass body of the redirecting arrangement 44, as shown in FIG. 5b is in the illumination beam path as well as in the measurement beam path, so that the measurement spot M is not illuminated. Illumination light enters perpendicular through one of the two inclined side surfaces 44d into the glass body and is reflected at its base surface 44a into the scattering layer 44b and there diffusely scattered. The diffusely scattered light exiting the scattering layer 44b is captured by the pick-up arrangement at an opening angle range of 0°+/−5° and guided to the spectrometer arrangement 30.

In the examples of FIGS. 5a and 5b, the illumination arrangement 10 includes only one light source 11. When instead two opposing light sources are used, their light enters through respectively one of the two opposing side surfaces 44d into the glass body.

The redirecting arrangement 44 in accordance with the invention is also easily adaptable to illumination arrangements with several light sources, as is shown in FIGS. 6a and 5b, for example, for four light sources in the form of light emitting diodes 11a to 11d positioned in a circle around the pick-up arrangement 20. The redirecting arrangement or the glass body 44 here are in the shape of a square pyramid frustum with four side surfaces respectively inclined at 45° to the base surface, through which the light of respectively one of the light sources enters into the glass body. It is understood that an extension to more, for example, six to eight inclined light entry surfaces is possible. In an extreme case, the glass body 44 can also be frusto-conical whereby its mantle then forms a theoretically infinite number of light entry surfaces.

FIG. 7 shows an embodiment in which the illumination arrangement 10 is constructed according to a preferred embodiment of the invention as an annular illumination arrangement which surrounds the pick-up arrangement 20. In this case, the glass body 44 also has a square (or possibly hexagonal or octagonal) layout.

The construction of the redirecting arrangement 44 as glass body in accordance with the invention is advantageous in many respects. The glass body consists of commercially available base material and can be manufactured at low costs as a single precise part. The glass and the flashed opal glass layer are very stable relative to temperature, humidity and time. The illumination of the measurement object (paper) and the flashed opal glass layer (cover layer after reflection on the mirrored base layer) are mostly the same. The optical path from the light source to the measurement object and to the opal glass layer is the same. The opal glass layer is a Lambert scatter unit and scatters the impinging light essentially at 45° (from above) into the full space angle, especially also upwards in direction of the lens head of the pick-up arrangement. The calibration measurement corresponds very exactly to a calibration on a conventional white tile in measurement plane position. The construction as a prism with trapezoid cross section or as a pyramid frustum allows the summation of the illumination strengths from two or more light sources. The glass body allows the individual coloration of white light emitting diodes and also of narrowband R G B light emitting diodes or light emitting diodes with narrowband converters. The glass body allows the coloration of light emitting diodes with polarizer, since the opal glass layer fully depolarizes. The redirecting arrangement in accordance with the invention can also be used in connection with the linear illumination described further below and it also allows for the calibration of a gloss measurement channel which is also further described further below.

Of course, the redirecting arrangement 44 could also be made of another transparent material (for example plastic) in combination with a suitable scattering layer (for example an injection mold process). The scatter layer can be formed analogous to the white flashed opal glass by a second (plastic) material homogenously connected with the transparent material or by a scattering surface structure of the transparent material. Instead of or in addition to the mirroring of the base surface, the base surface could also be constructed to be fully reflective.

It is understood that the brightness reference arrangement is absolutely standardized with the use of a precisely measured, conventional external white tile by way of a transfer calibration (in the robot during the manufacture and testing).

A further aspect of the invention relates to the construction of the illumination arrangement 10. An annular illumination arrangement as it is illustrated in FIG. 8 is especially suitable for use in the colour measurement device or especially the spectrophotometer. A large number of individual light emitting diode chips 11 are hereby densely packed and positioned in a small and narrowly defined annulus which coaxially surrounds the optical axis 21 of the pick-up arrangement 20. The typical size of the individual light emitting diode chips is about $0.4*0.4*0.4$ mm$^3$. The plane of the light emitting diode ring is perpendicular to the optical axis 21 and is thereby oriented parallel to the measurement plane.

The mechanical construction of the illumination arrangement 10 which is in this example ring-shaped is apparent from the cross-sectional illustration in FIG. 3. A circuit board 13 is positioned on a base plate 12 which is a good heat conductor and two coaxial annular walls 14 and 15 are positioned on the circuit board. An annular groove 13a is cut into the circuit board. The light emitting diode chips 11 are positioned in the groove 13a and directly adhered onto the base plate ("die bonding"). The electrical contacts of the light emitting diode chips are connected by way of not illustrated fine wires with corresponding contact surfaces on the circuit board 13 ("wire bonding"), which provides the connection to a here not illustrated external electronic control, whereby also a selective control of the individual light emitting diodes 11 and/or of groups of light emitting diodes 11 can be provided. The space between the two annular walls 14 and 15 is filled with a resin which includes a converter material (illuminant) for the conversion of certain wavelength ranges of the light emitted by the light emitting diodes into other wavelength ranges. This will be described in more detail further below. The illumination light is emitted from the surface of the cast resin 16 with cosine characteristic (Lambert emitter), which is indicated in FIG. 3 by arrow 17. The main direction of emission (radiation lobe) is thereby perpendicular to the plane of the light emitting diode ring.

The use of light emitting diodes (LED) as light sources for the illumination has many advantages. LEDs have a long service life and can be switched on and off quickly and in a very short time, whereby they are correspondingly energy efficient. By cycling the illumination and by differentiating between a measurement with the LEDs "on" and a following measurement with the LEDs "off" one can eliminate the auxiliary light influence during the measurement. LEDs do not emit heat radiation (IR) to the illuminated region. LEDs are available in specific spectral ranges, for example white, UV, R, G, B, etc. Typical commercially available light emitting diode products are Lumiled Emitter, Osram Golden Dragon, Cree Xlamp, etc.

In the circular illumination arrangement of FIG. 2, blue LED chips (at about 450 nm) and/or UV-LEDs (at about 390 nm) are used and together covered with a resin with converter (illuminant). A high light density is achieved by the dense population and small, narrowly defined line form.

The concept in accordance with the invention of the narrowly populated LED-line and the common casting of the LEDs with a converter containing resin is of course not limited to circular illumination arrangements. For example, a straight linear illumination arrangement can also be constructed according to the same principle, as it is required, for example, in line-by-line scanning devices.

Depending on the intended use, it can also be advantageous to position the light emitting diodes along a partially straight or otherwise curved line.

Relevant parts of an example of a line-by-line scanning device are illustrated in FIG. 10, whereby the longitudinal direction of the scanning device extends essentially perpendicular to the drawing plane. One recognizes linear, sequentially positioned pickup heads 20 an illumination arrangement with two straight linear LED lines 11a, 11b and the brightness reference arrangement with the sled 41 and the longitudinal, in cross-section trapezoid redirecting arrangement 44 in measurement position, which means outside the illumination and pick-up beam path.

The illumination concept in accordance with the invention with densely packed light emitting diode lines (straight or annular arrangement) enables the optimal adaptation of the illumination to specific application conditions. The illumination arrangement can be manufactured simply and cost efficiently with narrow tolerances.

For measurement technology reasons, an annular illumination is optimal for use in a point-by-point scanning spectrophotometer, since the preselected illumination geometry standards are best accomplished thereby while the highest light flow in the measurement spot is achieved at the same time. For line-by-line measurement apparatus, a line-shaped illumination with two symmetrically positioned illumination lines is optimal.

In the LED lines (linear or circular) different LED types (R, G, B, UV) can be positioned, according to a further preferred aspect of the invention, in regions (line portions or annular segments) and/or cast respectively with resin with different converter types, or possibly also completely without converter. For example, a region with individually switchable UV-LEDs without converter produces pure UW light for the controlled excitation and measurement of brighteners in the paper. A region with individually switchable R, G, B-LEDs without converter produces light in a narrow spectral range and is used for a controlled density measurement. (When one illuminates only in a narrow spectral region, the residual scattered light in the spectrometer is highly reduced.). Regions with switchable blue or UV-LEDs and cast with specific R, G, B converters also produce light in a narrow spectral range, which can be used for the controlled density measurement.

In the LED lines (linear or circular), different regions (line sections or annular segments) can be covered with different filters such as polarization, R, G, B or UV filters as is illustrated in FIG. 11. The filters are therein labeled with numeral 18. The illustrated four time symmetry is thereby preferred for reasons of measurement technology.

For example, a region with individually switchable LEDs which are covered by a polarization filter emits polarized light, another region with individually switchable LEDs without polarization filter emits unpolarized light. The switching from polarized to unpolarized light can thereby be carried out purely electrically by corresponding switching on and off of the respective LEDs, obviating complex mechanical switching. For this application, a crossed polarization filter must be rigidly integrated as analyzer in the pickup channel, which however is not of hindrance during unpolarized measurement.

Another region with switchable white LEDs which is covered with an R, G or B filter emits in a narrow spectral range and again serves for the improvement of the density measurement.

A further individually switchable region with UV filter allows, when very broadband white LEDs (with emission from 380 nm UV to 730 nm deep red) are used, an electrical on and off switching of the UV portion by control of the corresponding region.

The control of the LEDs in the individual regions of the illumination arrangement is carried out, as already mentioned, by way of an electronic control which possibly receives corresponding commands from a superior internal or external control.

Light emitting diodes suited for measurement technology use and converter materials suitable therefor are described in the technical literature and the data sheets of the pertinent manufacturers (for example Lumiled). An encompassing overview of the associated prior art was provided in a lecture "illuminants for white LEDs in the general illumination" by Dr. Stefan Tews (Litec LLL GmbH, Greifswald, Germany) as part of a VDI-conference in 2004.

White LEDs are used for the invention with YAG-illuminants or preferably ortho-silicate illuminants (BOSE) as converter (illuminant). These illuminants can be manufactured in different colours and can also be mixed, while the absorption and emission are spectrally separated. The illuminants can be pumped from blue (about 450 nm) to UV (about 390 nm).

According to page 25 of the lecture, the combination of a blue LED (452 nm) with two BOSE-LS-converters (blue-green, 508 nm and deep orange, 595 nm) provides a massive improvement compared to YAG. It is thereby important that the minimum between the LED emission maximum at about 450 nm and the converter emission above 500 nm is avoided as much as possible.

The "best" combination of a UV-LED with a mixture of various converters is illustrated on page 26 of the lecture. The spectrum is thereby well covered from 400 nm to 700 nm and the colour reproduction (colour rendering index) is excellent. The LED emits at 392 nm, and the converter types BAM (blue, 450 nm), BOSE (green, 515 nm), BOSE (orange, 593 nm) and silicate-germanate-LS (red, 657 nm) are used.

This LED converter combination is especially advantageous, since a UV LED is thereby used which can also be used as UV source for the specific excitation of paper brighteners.

In numerous applications of a colour measurement device or spectrophotometer, for example for the measurement of a printed sheet, the scanning must be contact free. The contact surface of the sheet over a relatively large area of the sheet is generally not perfectly even. Therefore, distance variations occur during scanning. They cannot influence the measurement results. This requires that the illumination arrangement and the pickup head must be distance independent over the tolerated range of a few tenths of millimeters.

The visual field of the pickup head is illuminated by the illumination arrangement. Since the angle of capture of the pickup head is very limited (according to the colour measurement standards only angles of capture of +/−5° are tolerable) the illumination or beam density in the measurement field is measured, which is independent from the distance. Therefore, the illumination arrangement only needs to produce a constant illumination strength which is independent from the distance.

A suitable solution for a distance independent illumination under 45° is described in the above already mentioned EP-A 1 507 134 (corresponding to U.S. patent application Ser. No. 10/894,797 of Jul. 20, 2004). A radiation source with a Lambert emission characteristic is thereby positioned parallel to the plane of the measurement field. The position of the radiation source relative to the measurement field is selected such that the light hits the measurement field at an angle of 45°. According to the basic photometric law, a distance insensitivity is thereby achieved over a range of distance variations which is sufficiently large for the practice.

The annular illumination arrangement according to the invention is constructed and positioned according to exactly the same principals. The distance independence is achieved when the plane of the light emitting diode ring is parallel to the measurement plane and a distance a of the ring from the measurement plane is selected to be equal with the radius r of the ring (FIG. 1). When the illumination arrangement is constructed as a linear light emitting diode line, the distance independence is fulfilled with sufficient approximation.

A further important aspect of the invention deals with the practical use of the colour measurement device: especially the spectrophotometer, for the determination (classification) of the quality (the type) of a measurement object—generally printing paper—by way of gloss measurement by using the photoreceptor 50 located opposite the illumination arrangement, the detection region of which is limited by an aperture to the measurement spot. The aperture is formed by a shutter 1b (FIG. 14) formed in the housing. The specially constructed brightness reference arrangement is again used for the calibration of the gloss channel. FIGS. 12 to 15 illustrate the conditions during the actual gloss measurement and during the calibration.

Quality determination is understood to refer to a classification of the paper (or generally the substrate) according to its reflection properties. It is therefore often only distinguished in practice between two paper qualities, namely "glossy" or "matt". It is obvious that principally the light reflected from the (unprinted) paper can be used for this distinction or classification. However, the photoreceptor 50 not only receives the reflected light but also a part of the light diffusely scattered or reemitted by the paper. This light portion must be subtracted for the absolute gloss measurement and the classification based thereon. One proceeds as follows in that respect:

Initially, a measurement spot on the unprinted paper is illuminated with white light. The diffusely scattered light (remission) is measured with the pick-up arrangement 20 and the connected spectrometer 30 (together referred to as "colour measurement channel") and the light reflected on the paper surface at 45° (reflection) is measured with the photoreceptor 50 (referred to as "reflex channel"). However, the reflex channel undesirably also measures, as already mentioned, the part of the light diffusely scattered by the paper (remission). This signal in the reflex channel is proportional to the illumination intensity which can be measured especially with the reflex channel by the insertion of the brightness reference.

During the standardization as well as in the practical measurement application one calculates with the ratio $Q_{Reflection}$ of the signal $S_{Reflection}$ in the reflex channel when the brightness reference is outside the beam path, which means during the measurement on the measurement object, and the signal $S_{Reflection\_0}$ when the brightness reference is in the beam path.

$$Q_{Reflection} = S_{Reflection}/S_{Reflection\_0}$$

The signal ratio $Q_{Reflection}$ of the reflex channel consists of two portions:

$$Q_{Reflection} = a*\text{Reflection} + b*\text{Remission},$$

whereby a and b are two parameters determined by standardization measurements. They are constants for a colour measurement device and determined by the geometry, essentially by the shape of the aperture. The parameters a and b are somewhat shifted in each colour measurement device because of tolerances and must therefore be individually determined for each colour measurement device during the standardization.

The aperture is selected in practice in such a way that for a typical white glossy paper the signal on the reflex sensor 50 is determined to about 50% by the remission and to about 50% by the reflection. The signal ratio 50:50 is not essential, since it is only important that the useful signal (reflection) does not disappear in the background noise relative to the undesired signal (remission).

The parameters a and b are determined during the standardization of the colour measurement device in the production by preferably robot controlled measurements on a black glossy tile (black glass, remission typically 0%, reflection typically 4%) and on a matt white tile (BCRA white, remission typically 90%, reflection typically 0%):

$$a = Q_{Reflection\_Black\ glass}/4\%,\ b = Q_{Reflection\_White}/90\%$$

$Q_{Reflection\_Black\ glass}$ herein refers to the measured signal ratio of the reflex channel during the measurement on the black tile and $Q_{Reflection\_BCRA\_White}$ the signal ratio of the reflex channel measured during the measurement on the white tile.

FIGS. 12 and 14 show the colour measurement device during the gloss measurement.

For the gloss measurement and the classification of the paper quality based thereon, only the absolute reflection (the absolute gloss) is of interest. When the factors a and b and the spectral remission measured in the spectral measurement channel are known, the absolute reflection (the absolute gloss) can be calculated as follows:

$$\text{Reflection} = (1/a)*Q_{Reflection} (b/a)*R$$

wherein $Q_{Reflection}$ means the measured signal ratio of the reflex channel and R the remission of the measurement object surface measured in the colour measurement channel (here spectral channel).

The relative sensitivities of the colour measurement channel (here spectral measurement channel) and the reflex channel must be calibrated both during the standardization and also during the gloss measurement, which is carried out according to an important aspect of the invention with the help of measurements on the white scattering layer 44b of the (device internal) brightness reference arrangement as is illustrated in FIGS. 13 and 15. The redirecting arrangement 44 is inserted into the beam paths. The spectral channel captures the light scattered upward by the scattering layer 44b, the reflex channel captures the light scattered downwards and to the right by the scattering layer 44b which reaches the photoreceptor 50 by way of the mirrored base surface and the right exit surface and through the aperture.

The determination of the absolute reflection and based thereon the classification of the substrate quality is carried out, for example, in a not further described stage of the control 100 of the spectrophotometer. It can of course also be carried out in a superior control or in a computer with which the spectrophotometer communicates (in a generally known manner).

Another important aspect of the invention deals with the further improvement of the further above-mentioned distance independence between measurement head and measurement object. During the contact free measurement of colours on substrates, for example by way of a measurement arrangement with 45°/0°-standard measurement geometry, a deviation from the nominal distance and angle between the measurement arrangement and the measurement object (substrate) leads to falsified measurement results. The main error component is the change of the illumination strength on the substrate and the thereby measured change in the remitted amount of light. Since the white calibration of the measurement arrangement is normally carried out during application on an internal or external brightness or white reference under standard conditions (which means under nominal distance and angle between measurement object and measurement arrangement), errors occur during the calculation of the remission of the substrate—essentially in the brightness (L), but also—mostly to a smaller degree—in the colour location (a, b). A change of the illumination strength on the measurement object upon a height or angle change results from the change of the distance between illumination light source and the measurement object, which is even the dominant error in simpler illumination arrangements (illumination strength is proportional to the square of the distance). A change of the illumination strength on the measurement object upon a height or angle change results further from the change of the actual illumination angles on the measurement object. The simpler the construction of the measurement optics, the larger this portion. With the annular illumination in accordance with the invention, this variation is relatively small, since the illumination strength is proportional to the cosine of the main angle of incidence. A change of the spectrum of the illumination upon a height or angle change occurs when the illumination system does not spectrally exactly homogenously illuminate the measurement object. This portion can be large, when the illumination light source radiates spectrally differently at different angles, which is especially the case with white LEDs. A change in the sensitivity of the pick-up channel occurs when the observed measurement spot changes in size and shape upon a change of height or angle.

The contact free measurement of different distances and angles between the measurement arrangement and the measurement object is of interest, for example, during the process control and/or control of the colour or spectral properties during the manufacture of materials such as paper, foils, ceramic, fabric, plastic, leather, etc. which are produced on the conveyor belt. It is further of interest with measurement devices which are adapted to measure one or two dimensional coloured test charts and with spectral or colour sensors which are used for photo control or adjustment of the colour in machines which are used for the printing of material. A contactless measurement is always required when the measurement object cannot be contacted on the surface to be measured, for example, because the printing colour is still wet or because the surface is sensitive. A contactless measurement is always a technical advantage when the construction can be simplified as a result. A contactless measurement is also a great technological advantage since thereby different substrate thicknesses (for example different paper qualities) and also uneven substrates (for example textured foils) can be measured.

For measurements on printed materials (measurement objects) of different thickness it is common today to eliminate the different distances between measurement surface and the measurement arrangement caused by different thicknesses of the printed material by a relative measurement. This means the measured values are related to the signal from the base substrate at the given distance (for example, to the white of the printed paper).

Although the measurement result is thereby independent from the distance, it is however dependent on the substrate used and can no longer be directly compared to measurement values based on other substrate materials.

A very good tolerance relative to distance variations is achieved with the further above-described construction and positioning of the illumination arrangement. The distance and angle independence can however be further improved with the additional measures in accordance with the invention described in the following. Although the previously described distance and angle tolerant construction of the illumination arrangement is advantageous, since the required corrections then remain smaller, it is however not a basic requirement.

The most basic underlying idea of the correction measures consists in a standardization of the spectral photometer (or any other colour sensor) for different measurement object distances (heights) and angles. An additional step is therefore inserted during the production of the colour sensor, more exactly during its standardization, during which the specific properties of each sensor produced are determined, during which additional step the height and/or angle dependency of each manufactured sensor is measured.

Figure 16A:
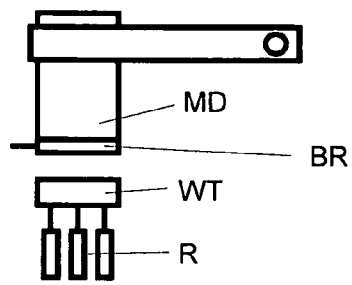
Figure 16B:
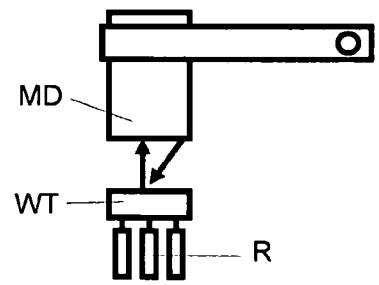
Figure 16C:
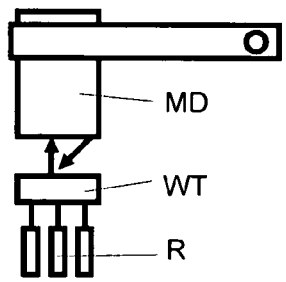
Figure 16D:
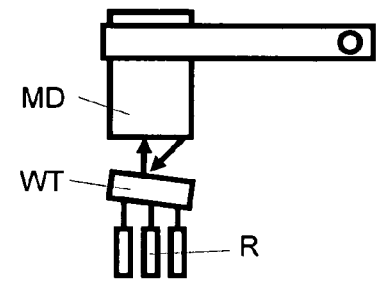

These standardization measurements can be carried out, for example, such that a reference probe (reference measurement object), preferably a very exactly measured white tile, is measured at different distances and/or angles to the sensor and the associated measurement data are stored in sensor (absolute white calibration). This is illustrated in FIGS. 16a to 16d. The colour sensor is referred to by MD. The reference measurement object is referred to by WT and is positioned at different distances and angle positions relative to the colour sensor MD by way of a measurement robot illustrated here only by three adjustable supporting members R. The relative white calibration of the sensor is carried out by way of the internal white reference built into the sensor, which is illustrated in FIG. 16a in the activated condition, which means inserted into the measurement beam path and is referred to by BR. This internal white reference consists in the present spectrophotometer of the described brightness reference arrangement.

Concretely, the absolute white calibration of the sensor during the manufacture is not only carried out exactly at standard height and standard angle, but according to the invention for a set of different heights and angles, whereby a total data set of calibration data results, which each typically consists of a white value for each colour or each spectral region (in the simplest case a one dimensional vector). The calibration data set is stored in association to the underlying distance and angle data, preferably in the sensor or its control.

FIG. 18 shows a principle schematic of the so expanded and improved spectrophotometer or generally colour sensor. Illustrated are the measurement head MD and a typically processor based control C of the colour sensor. The control C includes in addition to the control blocks C1 (control of the light sources, control of the photoelectric receptors, . . . ) present in each modern colour sensor and the conventional standardization and calibration data C2 the already mentioned set of distance and angle dependent calibration data C3. Furthermore, the control C can communicate by not illustrated interfaces with a superior control H, for example, it can receive command and control data H1 therefrom or send measurement data to the control H.

Figure 17A:
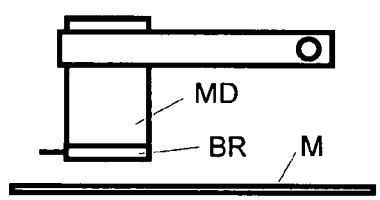
Figure 17B:
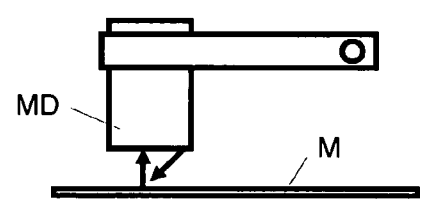
Figure 17C:
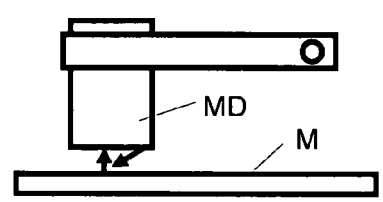
Figure 17D:
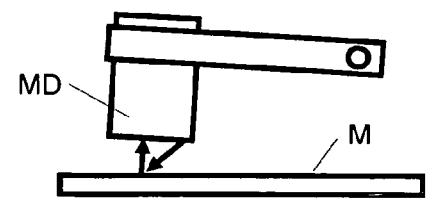

FIGS. 17a-d show the colour sensor in the practical measurement application in four different situations. In FIG. 17a, the internal white reference BR is activated for the relative white equalization. In FIG. 17b, the measurement plane M is at a nominal distance to the colour sensor MD. In FIG. 17c, the distance is smaller than the nominal distance and in FIG. 17d, the measurement head is tilted at a small angle relative to the measurement plane.

For the practical application of the measurement device (sensor) in an application device (not illustrated, for example a printer), one distinguishes between two cases: 1. distance and/or angle of the measurement object relative to the sensor are known (for example from the knowledge of the paper type used in a printer) and 2. distance and/or angle are not known.

In the first case, the distance and/or angle to the substrate is transmitted to the sensor in suitable form. This can be carried out, for example, by way of a command H1 of the superior control H (FIG. 18) through the communication interface of the sensor. In the exemplary concrete application of the colour sensor in a printing machine, the latter provides the distance and/or angle to the colour sensor.

By knowledge of the height and/or angle dependence given by the calibration data sets C3 previously stored in the sensor and with the transmitted actually present orientation between sensor and measurement object (distance, angle) the brightness of the colorimetric measurement result or the signal of the spectral measurement result is corrected. One thereby concretely uses the respectively fitting white vector for the calculation of the measurement data (remission spectrum or discrete remission values per color interval), which means the stored white vector C3 which was determined at the same height and the same angle during the original standardization. One interpolates, for example bi-linearly, between the nearest white vectors for not stored distance and angle values.

If it cannot be transmitted to the sensor under which geometric conditions the measurement will be carried out (case 2), the sensor is expanded according to the invention by an additional function C4 (FIG. 18) which allows it to determine the missing information itself. The distance measurement can be carried out, for example, by triangulation with the help of an additional optics. It is especially practical and advantageous according to a further aspect of the invention to adopt an approach wherein the signals of the spectral measurement channel are temporarily correlated with those of an additional measurement channel and a distance information is produced therefrom. The already present reflex channel used for the gloss measurements is thereby used as the additional measurement channel, so that no additional optical components are required for the distance measurement. This method and the associated means are further described in the following by way of the example of the spectrophotometer in accordance with the invention shown in FIGS. 19a-b and 20a-c.

FIG. 19 shows the spectrophotometer during the relative brightness calibration by way of the brightness reference arrangement or its redirecting arrangement 44 inserted into the beam path. In FIG. 19b, the spectrophotometer is ready for the measurement of a measurement object located in the measurement plane M. The two figures correspond to FIGS. 14 and 15 and therefore do not require any further explanation.

For the generation of the distance information, the spectrophotometer (or generally the colour sensor) is moved linear and parallel to the measurement object (for example paper) on the measurement plane, or the measurement object is moved under the spectrophotometer. A pattern, for example in the form of a black square Q (FIG. 19) is present, for example printed, on the measurement object. The pattern can be formed, for example, by a suitable field of the measurement object (for example a colour measurement chart). This pattern Q is recognized by the two measurement channels (spectral channel 20, 30 and reflex channel 50) as a function of the distance between the sensor and the measurement surface at different points in time. The FIGS. 20a-c show the measurement signal curves of the two measurement channels in three different situations. The continuous lines represent the signal curves of the spectral channel, the stippled lines those of the reflex channel. In FIG. 20a, the measurement object or its scanned surface is at the nominal distance from the sensor, in FIGS. 20b and 20c at a smaller or larger distance. The phase shift of the signal curves of the two channels forms a measure of the distance between the sensor and the measurement object and is determined in a further control module C4 of the control C of the spectrophotometer (or colour sensor) and recalculated into corresponding distance data (FIG. 18). These distance data are then again used for the selection of the associated white vector in the stored calibration data C3. It is understood that the determination of the distance to the measurement object can also be carried out with other means and measurement methods, for example by way of mechanical or capacitative distance sensors.

The above described distance/angle correction can be used for different sensors, for example spectrophotometers, colour emitters, densitometers, etc., and is suitable for measurements on different substrate types, for example paper, foils, ceramic, fabric, plastics, leather, etc.

The distance/angle correction can be carried out on different levels: either in the measurement device (sensor) itself or in a superior device, for example a printer or a computer to which the sensor is connected or in a control of a measurement device into which the sensor is integrated.

The above methods for the angle correction can also be used in the case of contact measurements, for example, if for any reason the angle and distance cannot be optimally adjusted. This is the case, for example, when the measurement head rolls on a substrate or rests thereon and takes up different angle positions which deviate from the nominal value (nodding movement of the measurement head) because of different substrate thicknesses.

With the distance and angle correction in accordance with the invention, the illumination light loss at nominal distance/ angle is compensated by calculation and a significant improvement of the absolute measurement precision is achieved thereby. Furthermore, a higher inter-instrument precision is achieved, which means the correspondence of the measurement results from the different sensors under identical not optimal angle and distance conditions is improved, since not all sensors behave the same at the same deviations from the nominal position, which is due to manufacturing tolerances, especially tolerances in the illumination when light emitting diodes are used.

The invention claimed is:

1. Measurement head for a colour measurement device with an illumination arrangement including at least one light source for illumination of a measurement object located in a measurement plane (M) under an angle of incidence of essentially 45°, with a pick-up arrangement for capturing of measurement light remitted from the measurement object under an angle of reflection of essentially 0° relative to the perpendicular to the measurement plane, with a photoelectric receiver arrangement for conversion of the measurement light captured by the pick-up arrangement into corresponding electrical signals and with a brightness reference arrangement, the measurement head comprising a redirecting arrangement in association with the brightness reference arrangement positionable into and removable from a beam path between the illumination arrangement and the pick-up arrangement and located at a relatively large distance relative to the measurement plane, which redirecting arrangement, when in the beam path redirects at least some of the light originating from the illumination arrangement, into the pick-up arrangement, and the redirecting arrangement constructed as a prism shaped, frusto-pyramidal or frusto-conical, essentially transparent body with a mirrored flat base surface, a scattering layer parallel thereto and at least one lateral light entry surface inclined at 45° relative to the base surface, whereby the base surface is positioned perpendicular to an optical axis of the pick-up arrangement and the scattering layer is directed towards the pick-up arrangement, and whereby the body is dimensioned in such a way that when inserted in the beam path, the light originating from the illumination arrangement enters into the body essentially perpendicular through the at least one light entry surface and is reflected on the base surface into the scattering layer;

wherein the brightness reference arrangement includes a sled that is movable in a direction transverse to the optical axis between a measurement position and a reference position; and wherein the redirecting arrangement is mounted on the movable sled.

2. Measurement head according to claim 1, wherein the redirecting arrangement is made of a white flashed opal glass with a transparent base layer and a homogeneously connected opal glass layer, whereby the scattering layer is formed by the opal glass layer of the white flashed opal glass.

3. Measurement head according to claim 1, wherein the redirecting arrangement is made of transparent plastic, whereby the scattering layer is formed by a homogeneously connected layer of a scattering, second plastic or by a scattering surface structure.

4. Measurement head according to claim 1, wherein the redirecting arrangement includes two symmetrically opposite light entry surfaces so that illumination light originating from two opposing light sources can be directed into the scattering layer.

5. Measurement head according to claim 1, wherein the redirecting arrangement includes four to eight light entry surfaces, so that light originating from several light sources can be directed into the scattering layer.

6. Measurement head according to claim 1, wherein the illumination arrangement includes a linear array of light emitting diodes, whereby many individual light emitting diode chips are tightly packed along a small, narrowly defined straight, partially straight, curved or circular line and at least partially cast with a resin in which at least regionally a converting material for the conversion of the light emitted by the light emitting diodes into other wavelength ranges is contained.

7. Measurement head according to claim 6, wherein the illumination arrangement includes light emitting diodes with different spectral characteristics.

8. Measurement head according to claim 6, wherein the illumination arrangement includes UV light emitting and non-UV light emitting regions, whereby the UV light is preferably suited for the excitation of brighteners in paper.

9. Measurement head according to claim 6, wherein the illumination arrangement has regions provided with colour filters.

10. Measurement head according to claim 1, wherein the illumination arrangement has regions provided with polarization filters.

11. Measurement head according to claim 6, wherein the illumination arrangement includes white emitting regions and narrowband emitting regions.

12. Measurement head according to claim 6, wherein the illumination arrangement includes regions with narrowband converter materials.

13. Measurement head according to claim 11, wherein the narrowband emitting regions of the illumination arrangement are adapted for colour density measurements.

14. Measurement head according to claim 6, wherein the illumination arrangement include ortho-silicate illuminants (BOSE) as converter materials.

15. Measurement head according to claim 6, wherein the light emitting diodes of the illumination arrangement are individually or group wise selectively controllable.

16. Measurement head according to claim 1, further comprising functionality for determining absolute gloss of the measurement object.

17. Measurement head according to claim 16, further comprising a color measurement channel and a gloss measurement channel, wherein the color measurement channel is associated with a photo receptor adapted to receive light reflected by the measurement object at essentially 45° and wherein the absolute gloss of the measurement object is determined by calculation from measurement signals of the colour measurement channel and measurement signals of the gloss measurement channel.

18. Measurement head according to claim 16, wherein the redirecting arrangement of the brightness reference arrangement is adapted the white calibration of the gloss measurement channel.

19. Measurement head according to claim 16, further comprising means for classification of a measurement object according to the determined absolute gloss.

20. Measurement head according to claim 1, further comprising correction means for correcting measurement values, said correction means depending on different distances, angles or distances and angles to the measurement object.

21. Measurement head according to claim 20, wherein the correction means includes a set of white calibration data (C3) determined during the standardization or during operation under defined and known conditions for a number of different distances and angle positions relative to a white reference (WT).

22. Measurement head according to claim 21, wherein the measured values are corrected on the basis of an actual distance and angle to the measurement object during measurement, wherein the correction means selects or calculates, by interpolation or extrapolation, from the set of white calibration data (C3), white calibration data associated with the actual distance and angle and uses the selected or calculated white calibration data to correct the measured values.

23. Measurement head according to claim 22, wherein the correction means are adapted to receive information on the actual distance and angle to the measurement object by way of a communication interface.

24. Measurement head according to claim 22, further comprising distance measurement means for determining the actual distance to the measurement object.

25. Measurement head according to claim 24, wherein the distance measurement means includes an additional measurement channel with a separate photoreceptor.

26. Measurement head according to claim 25, wherein the distance measurement means is constructed to determine the actual distance to the measurement object on the basis of face difference between measurement signal curves of the additional measurement channel and the colour measurement channel.

27. Measurement head according to claim 26, wherein the additional measurement channel is formed by a gloss measurement channel.

28. Measurement head according to claim 1, wherein the measurement head is constructed as a spectral measurement head and is equipped with a spectrometer arrangement with an entry slot for spectral splitting of the measurement light received through the entry slot and captured by the pick-up arrangement.

29. Measurement head according to claim 1, wherein the at least one light source is constructed as a cosine emitter and positioned such that its radiation lobe is essentially perpendicular to the measurement plane (M) and a distance of the light source from the optical axis of the pick-up arrangement is essentially the same as the distance of the light source from the measurement plane (M).

30. A colour measurement device including a measurement head according to claim 1, the colour measurement device further comprising an electronic control for controlling the illumination arrangement and forming digital measurement values from the electrical signals produced by the photoelectric receiver arrangement.

31. A colour measurement device according to claim 30, wherein said colour measurement device is a spectrophotometer.

* * * * *